United States Patent
Graupner et al.

(10) Patent No.: US 6,938,623 B2
(45) Date of Patent: Sep. 6, 2005

(54) CHILD SAFETY RESTRAINING DEVICE FOR USE WHERE A CHILD IS SEATED

(76) Inventors: Mashelle Anne Graupner, 12197 Cedarbreaks La., Cincinnati, OH (US) 45249; Glennon Harold Paul, 12197 Cedarbreaks La., Cincinnati, OH (US) 45249; Andrew A Paul, 12197 Cedarbreaks La., Cincinnati, OH (US) 45249

( * ) Notice: Subject to any disclaimer, the term of this patent is extended or adjusted under 35 U.S.C. 154(b) by 191 days.

(21) Appl. No.: 10/292,237

(22) Filed: Nov. 12, 2002

(65) Prior Publication Data

US 2004/0089311 A1 May 13, 2004

(51) Int. Cl.[7] .............................................. A61B 19/00
(52) U.S. Cl. ...................................... 128/869; 128/876
(58) Field of Search .............................. 128/869, 876, 128/878, 879, 882; 602/20, 27

(56) References Cited

U.S. PATENT DOCUMENTS

| | | | | |
|---|---|---|---|---|
| 2,721,420 A | * | 10/1955 | Chatten | ............................ 36/1 |
| 3,589,341 A | * | 6/1971 | Krebs | .......................... 119/865 |
| 4,422,455 A | * | 12/1983 | Olsen | .......................... 128/878 |
| 4,766,682 A | * | 8/1988 | Malloy, III | ................... 36/132 |
| 4,784,889 A | * | 11/1988 | Daniels | ....................... 428/100 |
| 4,948,117 A | * | 8/1990 | Burke | .......................... 482/55 |
| 5,263,726 A | | 11/1993 | Wood | |
| 5,378,046 A | | 1/1995 | Gordy et al. | |
| 5,641,200 A | | 6/1997 | Howell | |
| 5,678,888 A | | 10/1997 | Sowell et al. | |
| 5,918,891 A | | 7/1999 | Russell | |
| 6,095,613 A | | 8/2000 | Ostrander et al. | |
| 6,109,698 A | | 8/2000 | Perez | |
| 6,138,677 A | * | 10/2000 | DeVane | ....................... 128/869 |
| 6,186,521 B1 | | 2/2001 | Divoky et al. | |
| 6,206,471 B1 | | 3/2001 | McGowan | |
| 6,247,750 B1 | | 6/2001 | Tsai | |
| 6,250,680 B1 | | 6/2001 | Möker | |
| 6,409,272 B1 | | 6/2002 | Martin et al. | |

FOREIGN PATENT DOCUMENTS

| | | | |
|---|---|---|---|
| CA | 2071195 | A1 | 12/1993 |
| CA | 2071195 | * | 12/1993 |
| JP | 245106 | * | 9/2003 |
| JP | 2003-245106 | A | 9/2003 |

* cited by examiner

Primary Examiner—Michael A. Brown
(74) Attorney, Agent, or Firm—Andrew A Paul (57) ABSTRACT

A child safety restraining device comprising: (a) an ankle strap having a first end and a second end; (b) means for fastening the first end and the second end of the ankle strap to each other; (c) an anchor strap having a first end and a second end; (d) means for attaching the first end of the anchor strap and the ankle strap to each other; and (e) means for anchoring the second end of the anchor strap to an apparatus, e.g. a shopping cart, in which a child may be seated, at an anchoring point on the apparatus. Also provided are methods of using such a device to restrain seated children and increase their safety.

69 Claims, 6 Drawing Sheets

CHILD SAFETY RESTRAINING DEVICE FOR USE WHERE A CHILD IS SEATED

BACKGROUND OF THE INVENTION

This invention relates to safety devices for children. More particularly, it relates to child safety restraining devices for use where a child is seated, for example, a shopping cart, high-chair, stroller, infant seat, or similar apparatuses.

Shopping carts were introduced in the 1930's and in the following decades they were fitted with child seats, allowing child-caretakers more freedom to move about while placing the child in what was believed to be a relatively safe and immobile position. While it took a long time for adults to develop shopping carts, the period was brief before children figured out how to escape from child seats, and unknowingly place themselves in danger of falling or other bodily peril. Most shopping carts are presently equipped with a child carrier, either integral or retro-fitted, designed such that children are in a seated position, facing the driver of the cart, straddling a divider between the child's legs. This is also how many high-chairs, strollers, infant seats and other items in which children are seated, are designed, and thus the difficulties associated with restraining children in them are similar to those encountered with shopping carts.

Children often wiggle around in these seats and may reposition their legs so that both extend through the same side of the divider. This may allow the child to slip through and fall or slip through only partially and become stuck therein, thus either dangling or causing the entire cart or chair to fall over. Some shopping carts or like apparatuses are fitted with safety belts to restrain a child's movements. U.S. Pat. No. 5,378,046 (Gordy, et al.) describes a waist belt restraint. U.S. Pat. No. 5,263,726 (Wood) describes a safety belt that extends around the waist and also between the legs of a child. U.S. Pat. No. 5,641,200 (Howell) describes a child restraint seat including shoulder straps and lap straps that are crossed around a child. U.S. Pat. No. 6,186,521 (Divoky, et al.) describes a child restraint system with a pair of shoulder straps and a crotch strap. For high-chairs, U.S. Pat. No. 6,247,750 (Tsai) describes a waist belt.

The safety systems provided in the art, however, suffer from various shortcomings. Some are too complex for many consumers who desire simpler systems to operate. Complex systems may encourage non-use altogether, or may result in partial or incorrect use, which may be more harmful to the child than if no safety device were employed. Safety systems that only provide waist restraint may be compromised by children who manage to wiggle out of the waist strap and then may risk getting their necks caught in the strap. Still other safety systems have fastening means that are within the grasp of the child and such means are liable to be unfastened by the child being restrained or accompanying children. Accordingly, there remains a need to provide a child safety restraining device that is not unduly complex to properly operate, is more resistant to being wiggled-free from, is not likely to cause further risk if it is compromised, and/or is less susceptible to being unfastened by the child it is intended to protect or by accompanying children.

It is desirable to have safety systems that may be either permanently attached or removably attached to the apparatus in which the child is seated. Removable ones may be susceptible to theft; however, they may be removed and cleaned. Permanent ones reduce the opportunity for theft and avoid the need for caretakers to carry the systems with them wherever they go. The skilled person will necessarily consider the circumstances around which the use of the device is contemplated to determine whether to employ removable or permanent systems.

The applicants have found, surprisingly, that many of the above mentioned difficulties may be remedied with a child safety restraining device that restrains a child's legs at or near the ankle, anchoring the leg to the apparatus in which the child is seated. Such child safety restraining devices comprise an ankle strap having ends that can be fastened to each other, an anchor strap that can be attached to the ankle strap at one end and can be anchored to the apparatus at another end.

SUMMARY OF THE INVENTION

The present invention relates to a child safety restraining device comprising: (a) an ankle strap having a first end and a second end; (b) means for fastening the first end and the second end of the ankle strap to each other; (c) an anchor strap having a first end and a second end; (d) means for attaching the first end of the anchor strap and the ankle strap to each other; and (e) means for anchoring the second end of the anchor strap to an apparatus, e.g. a shopping cart, in which a child may be seated, at an anchoring point on the apparatus. The invention also relates to methods of using such a device to restrain seated children and increase their safety.

BRIEF DESCRIPTION OF THE DRAWINGS

FIG. 1 is a perspective view of a child being restrained in a partially shown apparatus 200 by an embodiment of child safety restraining device 10, wherein the apparatus is a shopping cart 200a.

DETAILED DESCRIPTION OF THE INVENTION

The present invention relates to a child safety restraining device comprising: an ankle strap, means for fastening the ends of the ankle strap to each other, an anchor strap, means for attaching an end of the anchor strap and the ankle strap to each other; and means for anchoring another end of the anchor strap to an apparatus, e.g. a shopping cart, in which a child may be seated, at an anchoring point on the apparatus. The invention also relates to methods of using such a device to restrain seated children and increase their safety. These and other features are described in detail below.

As used herein, the term "child" includes infants, toddlers, and other young children who may be placed in child seats by adults or other caretakers.

The descriptions of all references cited herein are incorporated by reference in their entirety, however the citing of any reference is by no way to be considered an admission that the same qualifies as prior art to the invention disclosed herein. Headings, paragraph breaks, and section breaks are used merely for convenience. Unless otherwise indicated, the articles "a" and "an" mean "one or more".

A. The Child Safety Restraining Device

Figure 1:
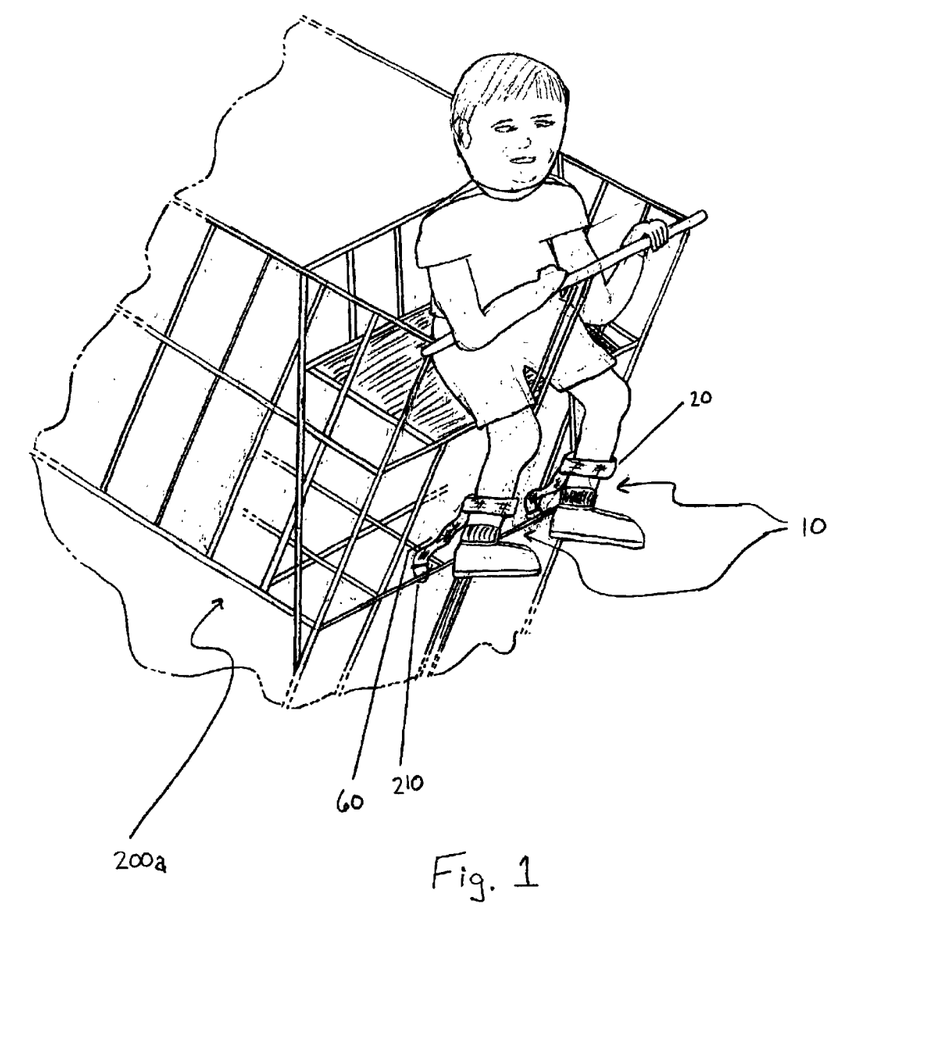

FIG. 1 shows a child being restrained in a partially shown apparatus 200 in which a child may be seated (the apparatus partially shown is shopping cart 200*a*) by an embodiment of child safety restraining device 10. Device 10 comprises an ankle strap 20 and an anchor strap 60, which are attached to each other, as described below. Anchor strap 60 is anchored to apparatus 200*a* at an anchor point 210 on the apparatus.

Apparatuses that are suitable for use herein are those in which a child may be seated and it may be desirable to restrict their unauthorized attempts to exit the seat. The seat itself may be formed integrally with the apparatus or it may be permanently or removably retrofitted. Non-limiting examples of such apparatuses are shopping carts, highchairs, strollers, and infant seats.

Figure 2:
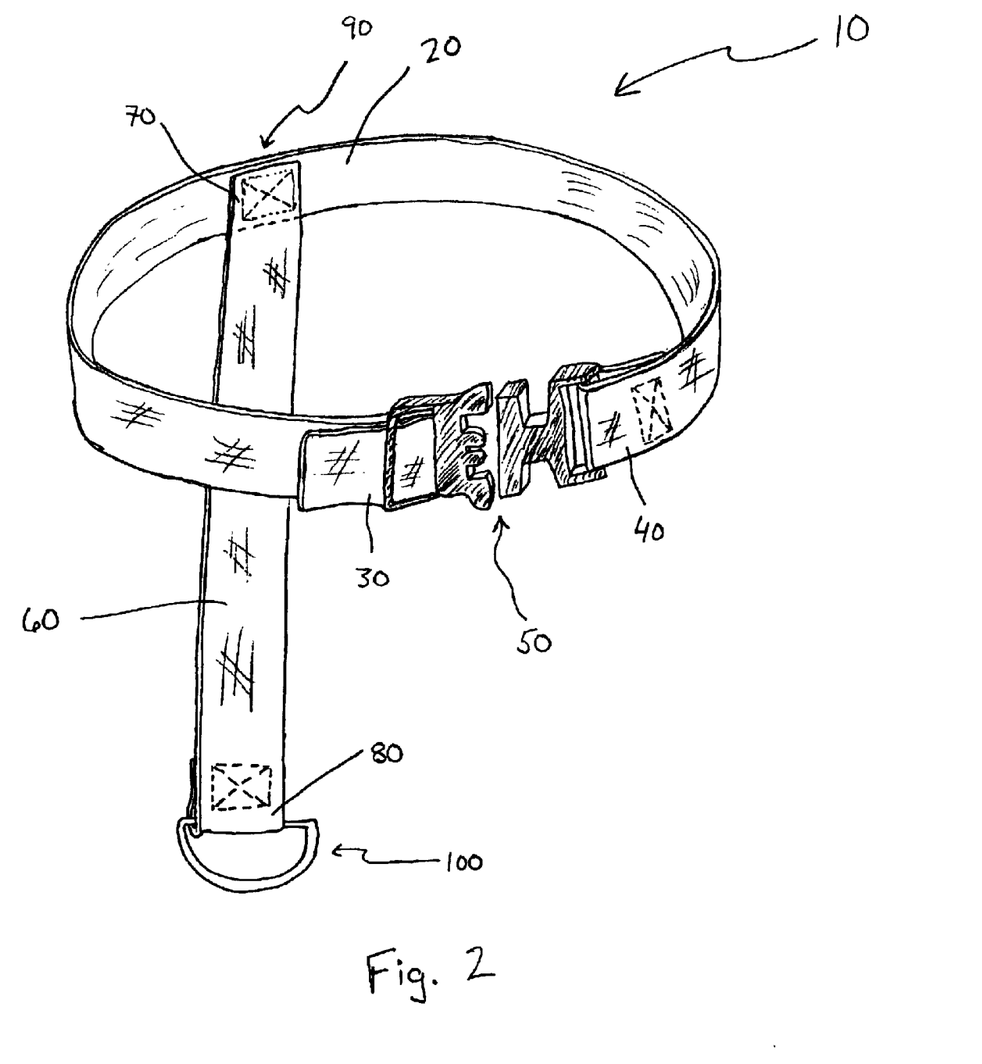
FIG. 2 is a perspective view of an embodiment of child safety restraining device 10.

FIG. 2 shows an embodiment of child safety restraining device 10. Ankle strap 20 has a first end 30 and second end 40. Device 10 also comprises means 50 for fastening first end 30 and second end 40 to each other. Anchor strap 60 has a first end 70 and a second end 80. Device 10 also comprises means 90 for attaching first end 70 and ankle strap 20 to each other. Device 10 also comprises means 100 for anchoring second end 80 to apparatus 200 (not shown in this Fig.) at an anchor point 210 (not shown in this Fig.) on the apparatus 200.

Ankle strap 20 is of sufficient length or is adjustable to such a length, to fit around a child's ankle comfortably, yet prevent the child from removing their ankle from the enclosure made by the strap when its ends are fastened to each other. It is not critical which of the ends of ankle strap 20 is designated "first end" or "second end". Suitable means 50 for fastening first end 30 and second end 40 to each other are described below.

Anchor strap 60 is of sufficient length or is adjustable to such a length, to permit a child's leg to move about comfortably, yet restrain the child in the seat in which they have been seated by anchoring device 10 to apparatus 200 at anchor point 210. Suitable means 90 for attaching first end 70 of the anchor strap 60 and the ankle strap 20 to each other are described below, as is the area for attaching to occur. Suitable means 100 for anchoring second end 80 to anchor point 210 are also described below.

For a shopping cart 200*a*, anchor point 210 may typically be a point along the gridwork of wires that comprise the shopping cart. For a high chair 200*b* (not shown), anchor point 210 may typically be a point along the legs or any structural bridge connecting legs of the chair. For a stroller 200*c* (not shown), anchor point 210 may typically be a point along the frame of the stroller chosen so as not to interfere with the operation of the wheels. However, for each of these apparatuses and others, any point that when anchored to, is useful generally in restraining the child and specifically is useful in preventing anchor strap 60 from being undesirably detached from the apparatus, is suitable for being anchor point 210. It will be apparent to those skilled in the art that the site selected for the anchor point 210 will vary with the type, design, and dimensions of the apparatus 200. It is also contemplated by the Applicants that where an apparatus does not already comprise a suitable site for the anchor point, such apparatus may be modified by conventional means to further comprise such a site. For example, a U-bolt or other ring-containing article may be retro-fitted onto the apparatus.

To accommodate for differences in the design and dimensions of various apparatuses 200, and also for differences in the dimension and activity of the child being restrained, the length of either strap 20, 60 may be fitted with any suitable length adjuster, such as those typically and conventionally used for adjusting the length of straps for tote bags, backpacks, hand luggage, video camera cases, and the like, wherein the strap is threaded through an adjuster and folded upon itself, with the adjuster being capable of sliding about the strap either increasing or decreasing the strap's length. The width of ankle strap 20 and anchor strap 60 may be selected independently, but they should be functionally and aesthetically compatible with each other. Preferably, the straps 20, 60 are shaped as substantially flat. When flat-shaped, each typically has a width of less than or equal to about 2 inches (about 5.1 cm), preferably less than or equal to about 1.5 inches (about 3.8 cm), more preferably less than or equal to about 1 inch (about 2.5 cm). The thickness of the straps will depend on the material selected and should also provide for functional and aesthetic compatibility.

In other embodiments, either or both of these straps may be shaped as cords. Typically the function of the anchor strap 60 makes it more accommodating to being shaped as a cord than the ankle strap 20, however where carefully done, it is possible to form ankle strap 20 as a cord also. Extra caution must be taken if the ankle strap 20 is shaped as a cord, as this may pose potential problems in use, e.g. due to risks involving reduced blood circulation and skin irritation, if applied too tightly around the child's ankle. When in the form of a cord, the cord will typically has an average diameter, including any coatings, of less than or equal to about 1 inch (about 2.5 cm), preferably less than or equal to about 0.75 inches (about 1.9 cm), preferably less than or equal to about 0.5 inches (about 1.3 cm), more preferably less than or equal to about 0.25 inches (about 0.6 cm).

B. Fastening Means

The means 50 for fastening the first and second ends 30, 40 of ankle strap 20 to each other may comprise any structure or combination of structures that are suitable for connecting and disconnecting the first end 30 and second end 40 in order to create and selectively release a loop comprising ankle strap 20 that encloses a child's ankle. Typically such means will permit a caretaker to connect and disconnect first and second ends 30, 40 of ankle strap 20 upon applying a reasonable amount of force, when desired, however will prevent a child (either the one being restrained or another assisting in the restrained child's unauthorized attempt to exit the seat) from doing the same. The structure (s) comprising such means may be dimensioned to reduce the discomfort it may cause against the child's ankle. For example, they may be curved to complement the contours of the ankle area.

Suitable fastening means for use herein include but are not limited to a coupler or coupler buckle, such as that described in U.S. Pat. No. 5,378,046 (Gordy, et al.), wherein one part of the coupler is a box side, with a retainer loop for the purpose of affixing permanently to one end of ankle strap 20, e.g. first end 30, by way of the first end 30 being put through the retainer loop and connected back on ankle strap 20 forming a closed loop. Non-limiting examples of permanent fixing include: weaving, braiding, stitching, riveting, gluing, stapling, clamping, and bolting. The other part of the coupler is a strap adjusting side, e.g. serpentine, which when another end of ankle strap 20, e.g. second end 40, is put into and through its ladder bars, allows for ankle strap 20 to be adjusted. Also suitable for use herein are two-part buckles and split key rings such as those described in U.S. Pat. No. 5,263,726 (Wood), wherein first end 30 is fitted to one part of the buckle or key ring, and second end 40 is fitted to the complimentary part of the buckle or key ring. Such buckles as described in Wood may be provided with means for permitting the length of the adjacent strap to be adjusted. In the embodiment of the invention shown in FIG. 2, fastening means 50 comprises a two-part buckle.

Figure 3:
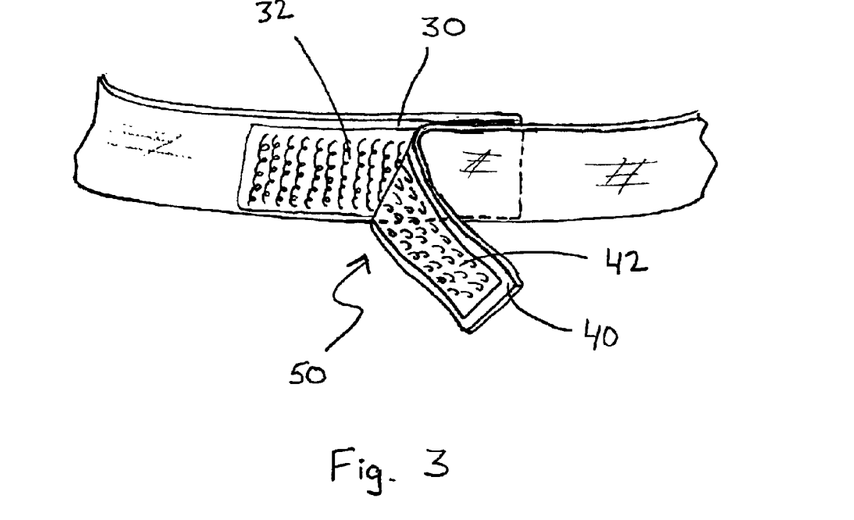
FIG. 3 is a partial view of an alternate embodiment of fastening means 50.

FIG. 3 shows a suitable embodiment of fastening means 50 involving a hook and loop system, e.g. VELCRO (trademark). An exterior surface area 32 of first end 30 and an interior surface area 42 of second end 40 may be provided with opposite textures (i.e. hook on area 32 and loop on area 42 or vice versa), such that when area 32 is aligned with and pressed against area 42 first and second ends 30 and 40 are fastened to each other.

Figure 4:
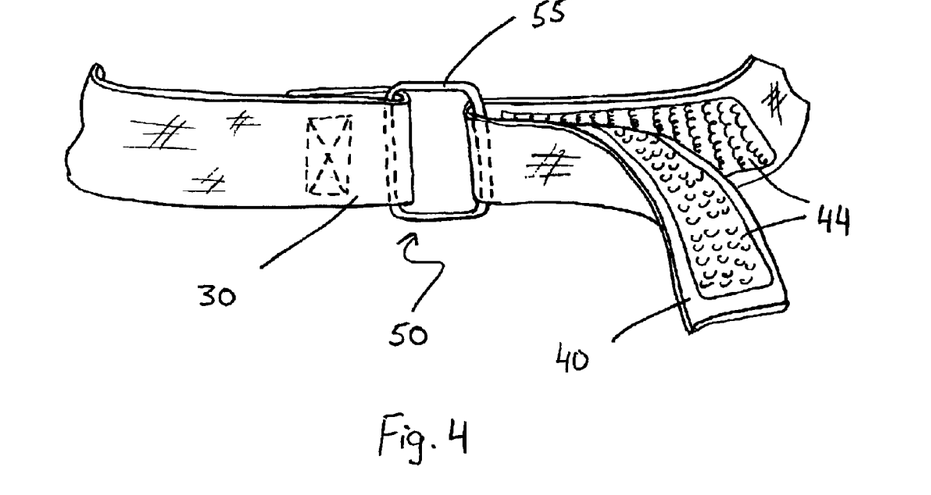
FIG. 4 is a partial view of another alternate embodiment of fastening means 50.

FIG. 4 shows a preferred embodiment of fastening means 50 involving a hook and loop system used in combination with retainer loop. A retainer loop 55 may be permanently affixed to first end 30. Suitable ways to permanently affix are described herein. An exterior surface area 44 of second end 40 may be provided with separate regions of opposite textures of the hook and loop system, such that when second end 40 is fed through the retainer loop 55 and folded back on itself, a substantial portion of the overlapping surface area comprises opposite textures of the hook and loop system, and the overlap portion stays fastened together.

When fastening means 50 comprises a hook and loop system, this advantageously allows easy fitting for various sizes of children's ankles, easy adjustment to correct erroneous sizing, and it presents a fastening means with low complexity for the user. Also suitable for use herein in similar fashion is a web-matching system, e.g. WEB-MATE (trademark), and a hook and loop system available as SCOTCHMATE (trademark) from Minnesota Mining and Manufacturing (USA). As used herein, a hook and loop fastening system refers to any fastening system wherein the "hook" portion comprises multiple, shaped engaging elements that project from a backing, such elements being typically shaped as hooks, "T's", "J's", or like shapes, and wherein the "loop" portion comprises multiple loops projecting from a backing, such loops typically being fibrous, and wherein the hook and loop portions engage one another to provide a secure, yet releasable fastening.

Still yet, other suitable fastening means 50 may comprise oppositely (or at least sufficiently dissimilar to cause strong attraction) polarized magnets, wherein one magnet may be placed inside a buckle part to which first end 30 is permanently affixed, and an oppositely polarized magnet may be placed inside a complimentary buckle part that is adjustably affixed to second end 40.

C. Attaching Means

The means 90 for attaching ankle strap 20 and anchor strap 60 to each other may comprise any structure or combination of structures that are suitable for connecting ankle strap 20 and first end 70 of anchor strap 60 to each other in a manner that keeps ankle strap 20 and anchor strap 60 attached to each other and allows second end 80 to be anchored to anchor point 210 such that the child's leg is sufficiently secured to the apparatus to prevent the child from undesirably exiting the seat. The attaching may occur at any part of ankle strap 20 where such attaching does not interfere with the performance of fastening means 50. In a preferred embodiment, anchor strap 60 will be attached so that its length is positioned substantially perpendicular to ankle strap 20, as is shown in FIG. 2.

Figure 5:
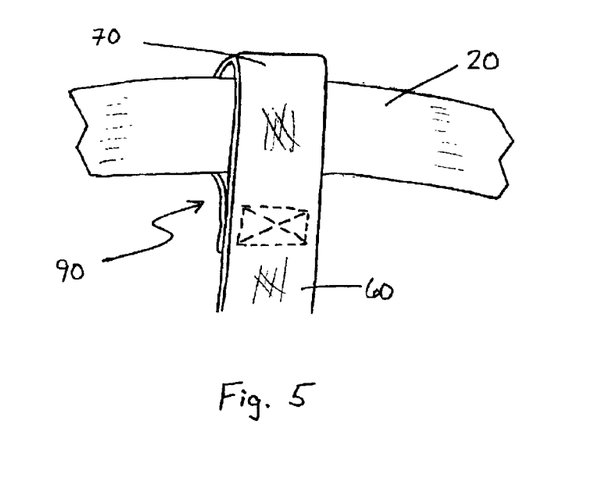
FIG. 5 is a partial view of an alternate embodiment of attaching means 90.

The attachment of ankle strap 20 and anchor strap 60 by attachment means 90 may be permanently fixed or non-permanently fixed, permanent fixing being preferred. For example, attachment may be made in a manner that prevents first end 70 from movement about the length of ankle strap 20, e.g. by permanently fixing first end 70 to a selected site along ankle strap 20, as is shown in FIG. 2, wherein first end 70 may be aligned with or folded over ankle strap 20, so that first end 70 either singly or doubly (not shown) overlaps ankle strap 20, whereupon the overlapping portion may be permanently fixed to ankle strap 20. Permanent fixing is described herein. Alternately, attachment may be made in a manner that permits first end 70 to move about, preferably slidably move about, a substantial length of ankle strap 20, e.g. by looping first end 70 over ankle strap 20 and back onto itself, whereupon the self-overlapping portion may be permanently fixed to anchor strap 60 at a location that allows the loop formed thereby to slide along ankle strap 20, as is shown in FIG. 5. Permanent fixing is described herein.

Figure 6:
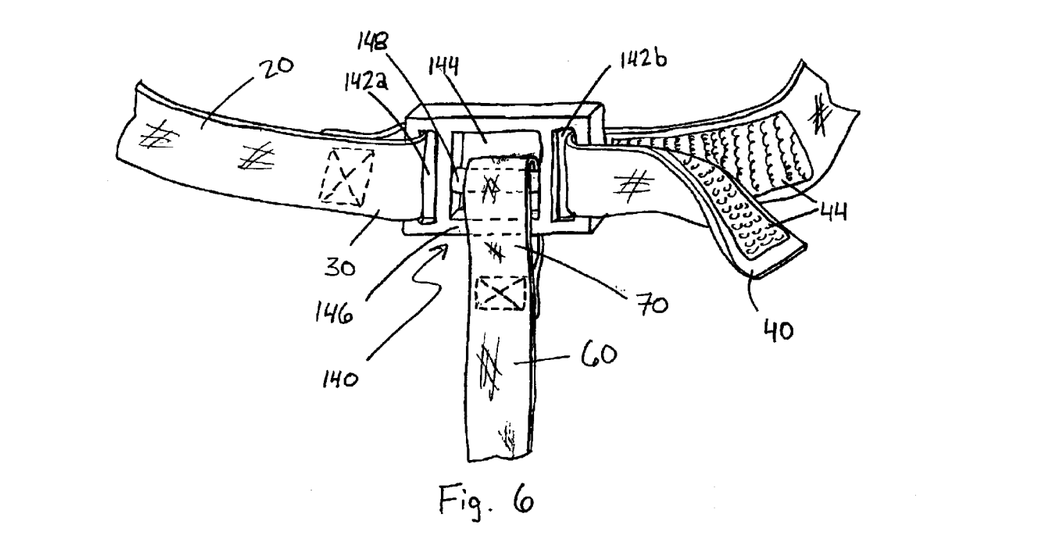
FIG. 6 is a partial view of another alternate embodiment of attaching means 90 formed integrally with fastening means 50.

In another preferred embodiment, fastening means 50 and attaching means 90 may be formed integrally, as shown in FIG. 6. As shown, fastening means 50 and attaching means 90 may comprise a T-coupler 140 that advantageously achieves the functions of both means 50, 90. In such an embodiment, T-coupler 140 may comprise two lateral retainer loop portions 142a, 142b which embody fastening means 50 and a medial retainer loop portion 144 which embodies attaching means 90. It is not critical which of the lateral retainer loop portions is designated as 142 "a" or "b". Lateral retainer loop portion 142a is dimensioned to allow first end 30 of ankle strap 20 to be permanently fixed to it, e.g. passing first end 30 through lateral retainer loop portion 142a, then folding first end 30 back on itself, forming a closed loop, which may then be permanently fixed as described herein. Lateral retainer loop portion 142b is dimensioned to allow second end 40 of ankle strap 20 to be adjustably fixed to it, e.g. an exterior surface area 44 of second end 40 may be provided with separate regions of opposite textures of the hook and loop system, such that when second end 40 is fed through lateral retainer loop portion 142b and folded back on itself, a substantial portion of the overlapping surface area comprises opposite textures of the hook and loop system, and the overlap portion stays fastened together. Medial retainer loop portion 144 is dimensioned to allow first end 70 of anchor strap 60 to be permanently fixed to it, e.g. passing first end 70 through medial retainer loop portion 144, then folding first end 70 back on itself, forming a closed loop, which may then be permanently fixed as described herein. The closed loop formed by the folding back of first end 70 may be allowed to rest directly on the base 146 of T-coupler 140, or in another embodiment, T-coupler 140 may further comprise a horizontal bar 148 spanning medial retainer loop portion 144, and the closed loop may be allowed to rest on the horizontal bar 148.

T-coupler 92 may be formed as a unitary piece or it may comprise subcomponents that are assembled. The Applicants contemplate that the T-coupler 92 may be functionally or aesthetically modified, for example, the edges and corners may be rounded or curved, the T-coupler itself may be curved, and any portion may be padded, as desired.

D. Anchoring Means

The means 100 for anchoring the second end 80 of anchor strap 60 to apparatus 200 at anchoring point 210 on the apparatus, may comprise any structure or combination of structures that are suitable for connecting (e.g. permanently anchored) or for connecting and disconnecting (e.g. removably anchored) second end 80 to, or to and from, anchoring point 210. Typically such means will permit a caretaker, store employee, or other responsible adult to connect or disconnect the straps, at the time desired, with a reasonable amount of effort, however will not permit a child (either the one being restrained or another assisting in the restrained child's unauthorized attempt to exit the seat) to do the same.

In one embodiment (not shown), suitable anchoring means comprises passing second end 80 through a part of the apparatus 200 at anchor point 210, folding the second end back onto anchor strap 60, and permanently or removably fixing the folded portion of second end 80 and anchor strap 60 to each other. Non-limiting examples of permanent fixing include: weaving, braiding, stitching, riveting, gluing, stapling, clamping, and bolting. Non-limiting examples of removable fixing include: tying, and providing the surfaces of folded portion and the anchor strap portion with opposite elements of a hook and loop or web-matching system.

In another embodiment, as shown in FIG. 2, suitable anchoring means 100 may comprise providing second end 80 with an anchor clip or ring that may be permanently or removably clipped to anchor point 210. Permanent attachment may be achieved by using a clip or ring that cannot be undone without destruction of the clip, e.g. a single-use clip or ring. Removable attachment may be achieved either by using a clip that is removed upon the application of sufficient force, e.g. the snap clip described in Gordy at col. 2, lines 37–40, and the D-clip described in U.S. Pat. No. 5,669,118 (Frano, et al.), or by using a clip that is removed upon being unlocked, the latter being useful in theft prevention.

Figure 7:
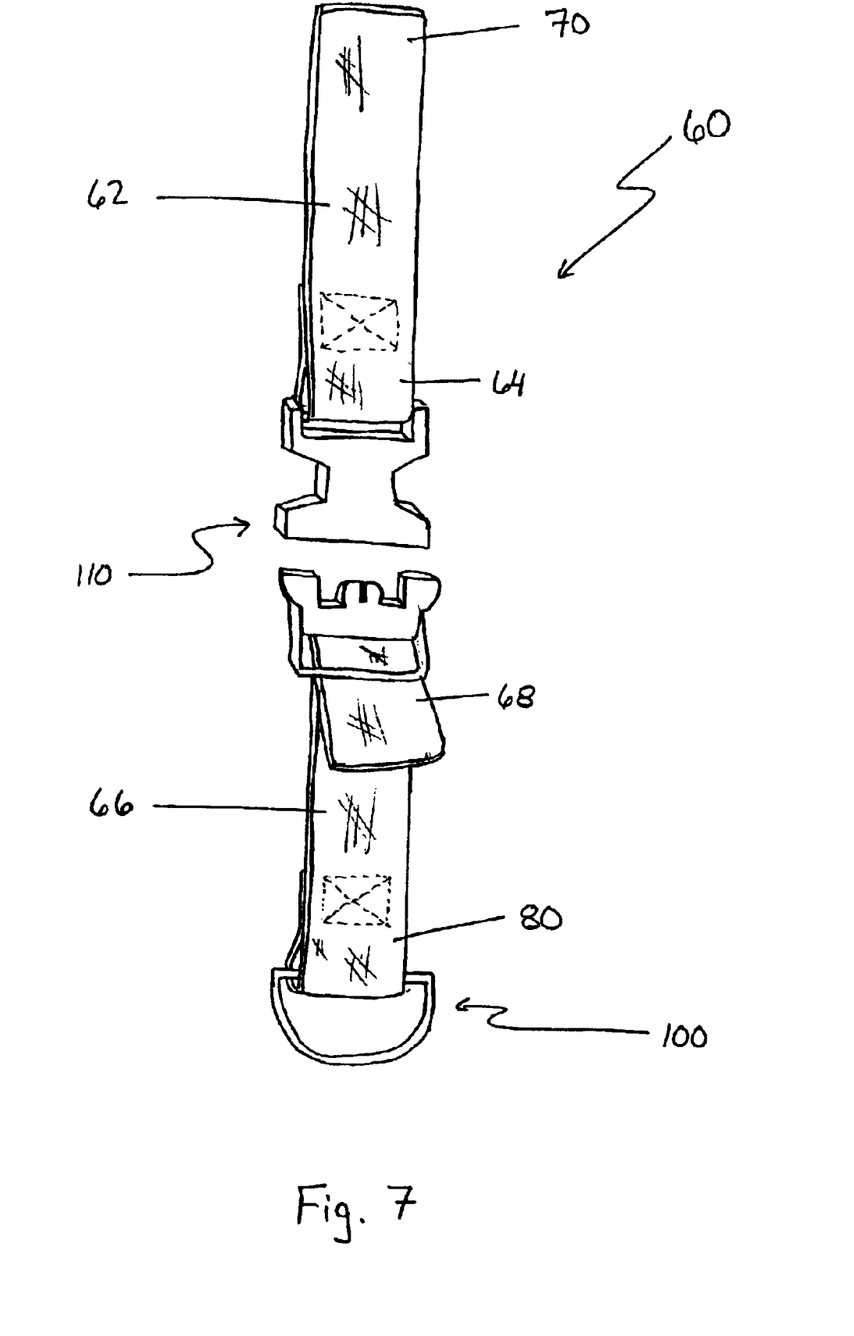
FIG. 7 is a perspective view of an alternate embodiment of anchor strap 60 having intermediate segments 62 and 66, and fastening means 110.

As shown in FIG. 7, in yet another embodiment, anchor strap 60 may comprise intermediate segments 62, 66 having medial ends 64, 68, respectively, and means 110 for fastening the medial ends 64, 68 to each other. By comprising intermediate segments and fastening means, anchor strap 60, in such an embodiment, it is advantageously provided that the adjustment of the length of anchor strap 60 is easily facilitated. It is also advantageously provided that the removal of a child from apparatus 200 is easily facilitated, e.g. the child may still be wearing all of device 10 save the portion including and between the part of fastening means 110 fixed to medial end 68, and anchor means 100. This latter advantage may be important especially in situations where rapid removal of the child is desired, e.g. emergency removal. Suitable fastening means 110 will comprise any means for fastening described herein as fastening means 50, wherein medial ends 64, 68 should be treated as first and second ends 30, 40.

Figure 8:
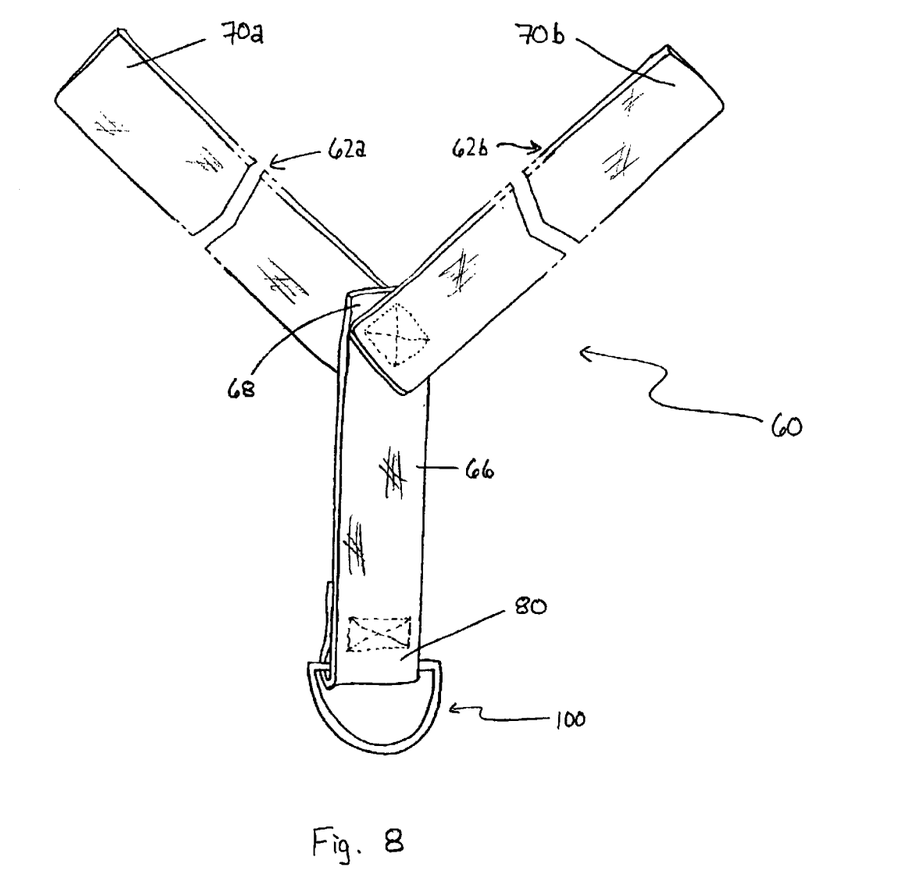
FIG. 8 is a perspective view of another alternate embodiment of anchor strap 60 in a "Y" conformation, having first ends 70a and 70b.

As shown in FIG. 8, in still another embodiment, anchor strap 60 may be formed in a "Y" shape, comprising first ends 70a, 70b. It is not critical which of the first ends is designated as 70 "a" or "b". By being formed as a "Y", anchor strap 60, in such an embodiment, it is advantageously provided that a single anchor strap 60 may anchor (via anchor means 100) two ankle straps 20a, 20b (not shown). As such, both of a child's legs may be safely restrained using a single device 10 that comprises two ankle straps 20a, 20b and a single anchor strap 60. The three intermediate segments of the "Y" 62a, 62b, 66, may be fixed permanently or non-permanently, as described herein.

E. Materials

The straps 20, 60 described herein may be made of any durable material or combination of materials. Preferably they are made of conventional materials that are not unduly burdensome to wash and/or disinfect, as needed, and which are appropriate for the environment, e.g. exposed to rain, snow or cold, that they will be used in. The straps may suitably be made from conventional fabrics, cotton, canvas, hemp, cloth, synthetic materials, e.g. nylon, vinyl, polyester, polypropylene, other synthetic polymeric materials, acrylic, DACRON (trademark), wool, leather, denim, and mixtures thereof. The straps may also be provided in the form of a cable or other cord. When made in cords, rubber may be suitable, or if the cords are metallic, then a rubber or other softer coating around the metal may be desirable. However formed, the straps may be provided with a covering that provides comfort against the skin of the child, and/or promotes hygienic use of the child safety restraining device. Such covering may be designed for single use, multiple use and then discard, multiple use and then cleaning and then re-use, or otherwise as will be apparent to those skilled in the art. Such covering may be formed integrally with the straps or may be coated upon them or may be attached to or around the straps. The straps may exhibit some bungee or elastic characteristics, but should be still be sufficiently strong to prevent escape by the child.

The structures or combinations of structures comprising fastening means 50, attaching means 90, anchoring means 100, and fastening means 110 may be made of any material suitable for fastening, attaching, or anchoring as described herein. Comfort against the skin of the child should be taken into consideration. Thus, the materials comprising these means may be selected so as to avoid providing undue discomfort to the child being restrained.

Any of the parts described herein may be padded, coated, or otherwise provided with a surface that contacts the child with added comfort, whilst maintaining functionality. Suitable coating materials include but are not limited to santoprene, thermoplastic polymeric materials, foam, rubber, flexible plastic, felt, and mixtures thereof.

F. Additional Features

Where suitable, any of the parts may be provided in any color, and with any form of printing, labelling, and design graphics. Advantageously, for example, advertising may be printed on the straps, e.g. to promote awareness of an event, a sale, a service, a candidacy, a slogan, or a product, or the identity of the owner of the device itself. Also, where a sponsor is providing the device for a caretaker's use, advertising may inform the caretaker of the benefactor who is funding the presence of the child safety restraining device. Furthermore, any of the parts may be glow-in-the-dark or otherwise may fluoresce. They may also be scented, e.g. with bubble-gum smell or other child-friendly smells or simply fresh-air scent, or they may be lighted, e.g. through the use of fiber optics.

The child safety restraining device may optionally be fitted with a noisemaker. The noisemaker may, in some embodiments, be turned on/off (and optionally sustained in the "on" mode, e.g. by battery operation) by a caretaker, or it may be actuated by the child's movement. Where actuated by the child's movement, the noisemaker may be used to provide an alert signal to the caretaker that the child is moving about, and where the noise generated is of a sufficient grade, it may indicate that the child is attempting to exit the seat in which they have been placed without authorization, thereby prompting a response from the caretaker or a helpful passerby. Alternately, regardless of the mode of actuation, the noisemaker may simply provide amusement for the child and those around them. Suitable noisemakers include but are not limited to bells, chimes, recorded sounds including words, sentences, phrases, songs, animal sounds and other noises, and the like.

Further variations may be made that will be obvious to one skilled in the art without departing from the scope or spirit of the invention.

G. Method of Making

The child safety restraining devices may be made by any conventional method. One simple method is to take a length of nylon strap material and cut two pieces to comprise the ankle strap and anchor strap. A first end of the ankle strap may be passed through a retainer loop, folded back on itself and stitched. A second end of the ankle strap may be provided with two opposite sections of a hook and loop fastening system. A piece of Velcro hooks plus backing may be aligned with a piece of Velcro loops plus backing on exterior surfaces of the second end, and then the two pieces may be individually sewn onto their respective parts of the exterior surface of the second end. This end will be passed through the retainer loop and fastened back on itself during use. Arranging the ankle strap and anchor strap in a substantially perpendicular fashion, a first end of the anchor strap may be aligned with a portion of the ankle strap that does not interfere with the operation of the hook and loop system plus retainer ring fastener that is provided to fasten the ends of the ankle strap to each other. The overlapping portion between the ankle strap and the anchor strap may be sewn together. The second end of the anchor strap may be passed through a D-clip, folded back on itself, and stitched. Making of the device may be adapted for automation or being performed on an assembly line as will be evident to those skilled in the art.

What is claimed:

1. A child safety restraining device comprising:
   (a) an ankle strap having a first end and a second end;
   (b) means for fastening said first end and said second end of said ankle strap to each other;
   (c) an anchor strap having a first end and a second end, wherein said anchor strap comprises two intermediate segments having medial ends and means for fastening said medial ends to each other;
   (d) means for attaching said first end of said anchor strap and said ankle strap to each other;
   (e) means for anchoring said second end of said anchor strap to an apparatus in which a child may be seated, at an anchoring point on said apparatus.

2. A device according to claim 1 wherein said apparatus is selected from the group consisting of a shopping cart, a high-chair, a stroller, and an infant seat.

3. A device according to claim 2 wherein said apparatus is a shopping cart.

4. A shopping cart comprising a child safety restraining device according to claim 1.

5. A device according to claim 1 wherein at least one of said straps further comprises a length adjuster.

6. A device according to claim 1 wherein at least one of said straps is shaped as substantially flat.

7. A device according to claim 1 wherein at least one of said straps is shaped as a cord.

8. A device according to claim 1 wherein said fastening means comprises a coupler.

9. A device according to claim 8 wherein said first end of said ankle strap is fitted to a first part of said coupler and said second end of said ankle strap is fitted to a second part of said coupler that is complimentary to said first part of said coupler.

10. A device according to claim 9 wherein said first part of said coupler comprises a retainer loop and said second part of said coupler allows the length of said ankle strap to be adjusted.

11. A device according to claim 8 wherein said coupler is formed as a two-part buckle.

12. A device according to claim 11 wherein said one part of said buckle comprises a magnet and said complimentary part of said buckle comprises an oppositely polarized magnet.

13. A device according to claim 1 wherein said fastening means comprises a hook and loop system.

14. A device according to claim 13 wherein said first end of said ankle strap is fitted with a hook portion of said hook and loop system and said second end of said ankle strap is fitted with a loop portion of said hook and loop system.

15. A device according to claim 14 wherein said fastening means further comprises a retainer loop.

16. A device according to claim 15 wherein said first end of said ankle strap is fitted to said retainer loop and an exterior surface of said second end of said ankle strap is fitted with separate regions of opposite textures of said hook and loop system, such that when said second end of said ankle strap is fed through said retainer loop and folded back on itself, a substantial portion of the overlapping surface area comprises opposite textures of said hook and loop system.

17. A device according to claim 1 wherein said fastening means comprises a web matching system.

18. A device according to claim 1 wherein said attaching means comprises said first end of said anchor strap and an overlapping portion of said ankle strap being fixed to each other.

19. A device according to claim 18 wherein said ankle strap and said anchor strap are oriented substantially perpendicular to each other.

20. A device according to claim 1 wherein said attaching means comprises said first end of said anchor strap being looped over said ankle strap and back onto itself, the self-overlapping portion of said first end of said anchor strap being fixed to said anchor strap.

21. A device according to claim 1 wherein said anchoring means comprises said second end of said anchor strap being passed through a part of said apparatus at said anchoring point and back onto itself, the self-overlapping portion of said second end of said anchor strap being fixed to said anchor strap.

22. A device according to claim 1 wherein said anchoring means comprises said second end of said anchor strap being provided with a "D"-shaped anchoring member capable of being fixed to said anchoring point.

23. A device according to claim 22, wherein said D-shaped anchoring member is selected from the group consisting of a D-clip and a D-ring.

24. A device according to claim 1 wherein at least one strap is made from a material selected from the group consisting of cotton, canvas, hemp, cloth, nylon, vinyl, polyester, polypropylene, acrylic, wool, leather, denim, and combinations thereof.

25. A device according to claim 1 wherein at least one component is coated with a material selected from the group consisting of santoprene, thermoplastic polymeric materials, foam, rubber, flexible plastic, felt, and combinations thereof.

26. A device according to claim 1 wherein at least one component is provided with printing, labelling, or design graphics.

27. A device according to claim 26 wherein said printing, labelling, or design graphics comprise an advertisement or an informative communication.

28. A device according to claim 1 further comprising a noisemaker.

29. A device according to claim 28 wherein said noisemaker is actuated by the movement of a child being restrained by said device.

30. A method of restraining a seated child comprising the steps of:
   (a) identifying a child seated in an apparatus in which a child may be seated; and
   (b) applying a device according to claim 1 to said child, comprising, in any order, the steps of:
      (i) placing said ankle strap around an ankle of said child and fastening said first end and said second end of said ankle strap to each other; and
      (ii) anchoring said anchor strap to said apparatus.

31. A method according to claim 30 wherein step (b)(ii) is performed by a person other than the person performing step (b)(i), and step (b)(ii) is performed before step (b)(i).

32. A method of increasing the safety of a seated child comprising the steps of:
   (a) identifying a child seated in an apparatus in which a child may be seated; and
   (b) applying a device according to claim 1 to said child, comprising, in any order, the steps of:
      (i) placing said ankle strap around an ankle of said child and fastening said first end and said second end of said ankle strap to each other; and
      (ii) anchoring said anchor strap to said apparatus.

33. A child safety restraining device comprising:
   (a) an ankle strap having a first end and a second end;
   (b) means for fastening said first end and said second end of said ankle strap to each other;
   (c) an anchor strap having a first end and a second end;
   (d) means for attaching said first end of said anchor strap and said ankle strap to each other;
   (e) means for anchoring said second end of said anchor strap to an apparatus in which a child may be seated, at an anchoring point on said apparatus.
   wherein said fastening means and said attaching means are formed integrally, said integrally formed means comprising a T-coupler, said T-coupler comprising two lateral retainer loops and a medial retainer loop;
   wherein said first end of said ankle strap is fitted to a first lateral retainer loop, said second end of said ankle strap is fitted to a second lateral retainer loop, and said first end of said anchor strap is fitted to said medial retainer loop;
   wherein the fastening means portion of said integrally formed means comprises a hook and loop system; and
   wherein an exterior surface of said second end of said ankle strap is fitted with separate regions of opposite textures of said hook and loop system, such that when said second end of said ankle strap is fed through said second lateral retainer loop and folded back on itself, a substantial portion of the overlapping surface area comprises opposite textures of said hook and loop system.

34. A device according to claim 33 wherein said medial retainer loop further comprises a horizontal bar, spanning said medial retainer loop.

35. A device according to claim 33 wherein the attaching means portion of said integrally formed means comprises said first end of said anchor strap being passed through said medial retainer loop and back onto itself, the self-overlapping portion of said first end of said anchor strap being fixed to said anchor strap.

36. A device according to claim 33 wherein said T-coupler is formed as a unitary piece.

37. A device according to claim 33 wherein said T-coupler comprises subcomponents that are assembled.

38. A device according to claim 33 wherein said apparatus is selected from the group consisting of a shopping cart, a high-chair, a stroller, and an infant seat.

39. A device according to claim 38 wherein said apparatus is a shopping cart.

40. A shopping cart comprising a child safety restraining device according to claim 33.

41. A device according to claim 33 wherein at least one of said straps further comprises a length adjuster.

42. A device according to claim 33 wherein at least one of said straps is shaped as substantially flat.

43. A device according to claim 33 wherein at least one of said straps is shaped as a cord.

44. A device according to claim 33 wherein said ankle strap and said anchor strap are oriented substantially perpendicular to each other.

45. A device according to claim 33 wherein the attaching means portion of said integrally formed means comprises said first end of said anchor strap being passed through said medial retainer loop and back onto itself, the self-overlapping portion of said first end of said anchor strap being fixed to said anchor strap.

46. A device according to claim 33 wherein said T-coupler is formed as a unitary piece.

47. A device according to claim 33 wherein said T-coupler comprises subcomponents that are assembled.

48. A device according to claim 33 wherein said anchoring means comprises said second end of said anchor strap being passed through a part of said apparatus at said anchoring point and back onto itself, the self-overlapping portion of said second end of said anchor strap being fixed to said anchor strap.

49. A device according to claim 33 wherein said anchoring means comprises said second end of said anchor strap being provided with a "D"-shaped anchoring member capable of being fixed to said anchoring point.

50. A device according to claim 49 wherein said D-shaped anchoring member is selected from the group consisting of a D-clip and a D-ring.

51. A device according to claim 33 wherein at least one strap is made from a material selected from the group consisting of cotton, canvas, hemp, cloth, nylon, vinyl, polyester, polypropylene, acrylic, wool, leather, denim, and combinations thereof.

52. A device according to claim 33 wherein at least one component is coated with a material selected from the group consisting of santoprene, thermoplastic polymeric materials, foam, rubber, flexible plastic, felt, and combinations thereof.

53. A device according to claim 33 wherein at least one component is provided with printing, labelling, or design graphics.

54. A device according to claim 53 wherein said printing, labelling, or design graphics comprise an advertisement or an informative communication.

55. A device according to claim 33 further comprising a noisemaker.

56. A device according to claim 55 wherein said noisemaker is actuated by the movement of a child being restrained by said device.

57. A method of restraining a seated child comprising the steps of:
   (a) identifying a child seated in an apparatus in which a child may be seated; and
   (b) applying a device according to claim 33 to said child, comprising, in any order, the steps of:
      (i) placing said ankle strap around an ankle of said child and fastening said first end and said second end of said ankle strap to each other; and (ii) anchoring said anchor strap to said apparatus.

58. A method according claim 57 wherein step (b)(ii) is performed by a person other than the person performing step (b)(i), and step (b)(ii) is performed before step (b)(i).

59. A method of increasing the safety of a seated child comprising the steps of:
   (a) identifying a child seated in an apparatus in which a child may be seated; and
   (b) applying a device according to claim 33 to said child, comprising, in any order, the steps of:
      (i) placing said ankle strap around an ankle of said child and fastening said first end and said second end of said ankle strap to each other; and
      (ii) anchoring said anchor strap to said apparatus.

60. A child safety restraining device comprising:
   (a) an ankle strap having a first end and a second end;
   (b) means for fastening said first end and said second end of said ankle strap to each other;
   (c) an anchor strap having a first end and a second end;
   (d) means for attaching said first end of said anchor strap and said ankle strap to each other;
   (e) means for anchoring said second end of said anchor strap to an apparatus in which a child may be seated, at an anchoring point on said apparatus;
   wherein said anchor strap is formed in a "Y" shape, said ankle strap and a first arm of said "Y" being attached to each other, and wherein said device further comprises: (i) a second ankle strap having a first end and a second end; (ii) means for fastening said first end and second end of said second ankle strap to each other; (iii) and means for attaching said second ankle strap and a second arm of said "Y" to each other.

61. A method of restraining a seated child comprising the steps of:
   (a) identifying a child seated in an apparatus in which a child may be seated; and
   (b) applying a device according to claim 60 to said child, comprising, in any order, the steps of:
      (i) placing said ankle strap around an ankle of said child and fastening said first end and said second end of said ankle strap to each other; and
      (ii) anchoring said anchor strap to said apparatus.

62. A method according to claim 61 wherein step (b)(ii) is performed by a person other than the person performing step (b)(i), and step (b)(ii) is performed before step (b)(i).

63. A method of increasing the safety of a seated child comprising the steps of:
   (a) identifying a child seated in an apparatus in which a child may be seated; and
   (b) applying a device according to claim 60 to said child, comprising, in any order, the steps of:
      (i) placing said ankle strap around an ankle of said child and fastening said first end and said second end of said ankle strap to each other; and
      (ii) anchoring said anchor strap to said apparatus.

64. A child safety restraining device comprising:
   (a) an ankle strap having a first end and a second end;
   (b) an anchor strap having a first end and a second end;
   (c) a T-coupler comprising two lateral retainer loops and a medial retainer loop, wherein:
      (i) said first end of said ankle strap is fitted to a first lateral retainer loop, said second end of said ankle strap is fitted to a second lateral retainer loop, and said first end of said anchor strap is fitted to said medial retainer loop;
      (ii) an exterior surface of said second end of said ankle strap is fitted with separate regions of opposite textures of a hook and loop system, such that when said second end of said ankle strap is fed through said second lateral retainer loop and folded back on itself, a substantial portion of the overlapping surface area comprises opposite textures of said hook and loop system;
      (iii) said first end of said anchor strap is passed through said medial retainer loop and back onto itself, and the self-overlapping portion of said first end of said anchor strap is fixed to said anchor strap; and
      (iv) said second end of said anchor strap is provided with an anchoring D-clip capable of being fixed to an apparatus in which a child may be seated, at an anchoring point on said apparatus.

65. A device according to claim 64 wherein said T-coupler is formed as a unitary piece.

66. A device according to claim 64 wherein said T-coupler comprises subcomponents that are assembled.

67. A method of restraining a seated child comprising the steps of:
   (a) identifying a child seated in an apparatus in which a child may be seated; and
   (b) applying a device according to claim 64 to said child, comprising, in any order, the steps of:
      (i) placing said ankle strap around an ankle of said child and fastening said first end and said second end of said ankle strap to each other; and
      (ii) anchoring said anchor strap to said apparatus.

68. A method according to claim 67, wherein step (b)(ii) is performed by a person other than the person performing step (b)(i), and step (b)(ii) is performed before step (b)(i).

69. A method of increasing the safety of a seated child comprising the steps of:
   (a) identifying a child seated in an apparatus in which a child may be seated; and
   (b) applying a device according to claim 64 to said child, comprising, in any order, the steps of:
      (i) placing said ankle strap around an ankle of said child and fastening said first end and said second end of said ankle strap to each other; and
      (ii) anchoring said anchor strap to said apparatus.

* * * * *